US012650380B2

(12) United States Patent
Wang et al.

(10) Patent No.: US 12,650,380 B2
(45) Date of Patent: Jun. 9, 2026

(54) METHODS AND RELATED ASPECTS FOR MOLECULAR TRACKING AND ANALYSIS

(71) Applicant: ARIZONA BOARD OF REGENTS ON BEHALF OF ARIZONA STATE UNIVERSITY, Scottsdale, AZ (US)

(72) Inventors: Shaopeng Wang, Chandler, AZ (US); Yunlei Zhao, Village Circle, IL (US); Guangzhong Ma, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 707 days.

(21) Appl. No.: 18/180,228

(22) Filed: Mar. 8, 2023

(65) Prior Publication Data

US 2023/0288331 A1     Sep. 14, 2023

Related U.S. Application Data

(60) Provisional application No. 63/319,208, filed on Mar. 11, 2022.

(51) Int. Cl.
*G01N 21/51* (2006.01)
*B82Y 15/00* (2011.01)
(Continued)

(52) U.S. Cl.
CPC .............. *G01N 21/51* (2013.01); *B82Y 15/00* (2013.01); *G01N 15/0211* (2013.01);
(Continued)

(58) Field of Classification Search
CPC ............. G01N 33/543; G01N 33/5308; G01N 33/54313; G01N 33/54333;
(Continued)

(56) References Cited

U.S. PATENT DOCUMENTS 5,698,397 A * 12/1997 Zarling .............. G01N 21/6454
435/7.1
7,122,384 B2 * 10/2006 Prober ............. G01N 33/54346
435/7.1
(Continued)

FOREIGN PATENT DOCUMENTS

WO     WO-2008008785 A2 * 1/2008     ........... G01N 33/588
WO     WO-2017090018 A1 * 6/2017     ............... C01G 7/00
WO     WO-2021008708 A1 * 1/2021     ............. G01N 30/74

OTHER PUBLICATIONS

Alvarez, Natalia et al., "Implementation and comparison of dynamic and static light scattering techniques for polidisperse particle sizing using a CCD camera," Journal of Physics: Conference Series 274 02134, pp. 1-8. (Year: 2011).*
(Continued)

*Primary Examiner* — Gordon J Stock, Jr.
(74) *Attorney, Agent, or Firm* — MH2 Technology Law Group LLP

(57)     ABSTRACT

Provided herein are methods of determining molecular binding kinetics on particles, such as magnetic nanoparticles. In some embodiments, the methods include introducing an incident light from a light source toward a sample container that comprises a particle-bound biomolecule-ligand composition comprising a plurality of particle-bound biomolecules and a plurality of ligands that binds, or is capable of binding, to biomolecules of the plurality of particle-bound biomolecules, detecting light scattered from particle-bound biomolecule-ligand complexes in the particle-bound biomolecule-ligand composition over a duration to produce a set of imaging data using the detector, and determining size or volume changes of one or more of the particle-bound biomolecule-ligand complexes during at least a portion of the duration from the set of imaging data to thereby deter-
(Continued)

mine the molecular binding kinetics on the particles. Related systems and computer readable media are also provided.

20 Claims, 11 Drawing Sheets

(51) Int. Cl.

| | |
|---|---|
| *G01N 15/0205* | (2024.01) |
| *G01N 15/0227* | (2024.01) |
| *G01N 15/10* | (2024.01) |
| *G01N 15/1433* | (2024.01) |
| *G01N 33/543* | (2006.01) |

(52) U.S. Cl.

CPC ..... *G01N 15/0227* (2013.01); *G01N 15/1433* (2024.01); *G01N 33/54326* (2013.01); *G01N 2015/0222* (2013.01); *G01N 2015/1029* (2024.01); *G01N 2201/0461* (2013.01); *G01N 2201/0484* (2013.01); *G01N 2201/067* (2013.01); *G01N 2201/102* (2013.01); *G01N 2201/122* (2013.01)

(58) Field of Classification Search

CPC ......... G01N 33/5434; G01N 33/54346; G01N 33/54326; G01N 15/00; G01N 15/02; G01N 15/0205; G01N 15/0211; G01N 15/0227; G01N 15/10; G01N 15/14; G01N 15/1434; G01N 15/1436; G01N 2015/0038; G01N 2015/0222; G01N 2015/0238; G01N 2015/025; G01N 2015/0277; G01N 2015/03; G01N 2015/035; G01N 2015/1029; G01N 2015/1493; G01N 2446/00; G01N 2446/10; G01N 2446/20; G01N 2446/80; G01N 2446/86; G01N 2446/90; G01N 2446/84; G01N 21/47; G01N 21/4738; G01N 21/4795; G01N 21/49; G01N 21/51; G01N 21/53; G01N 21/532; G01N 21/534; G01N 21/553; G01N 21/554; G01N 2021/4726; G01N 2021/4728; G01N 2021/4733; G01N 2021/4769; G01N 2021/4773; G01N 2021/513; G01N 2201/04; G01N 2201/0461; G01N 2201/0484; G01N 2201/067; G01N 2201/102; G01N 2201/10; G01N 2201/122; G01N 2201/1222; G01N 2201/1224; G01N 2201/1226; G01N 2201/1228; G01N 15/1433; B82Y 15/00

See application file for complete search history.

(56) References Cited

U.S. PATENT DOCUMENTS

| | | | | |
|---|---|---|---|---|
| 8,883,094 | B2 * | 11/2014 | Huo | G01N 33/542 |
| | | | | 356/246 |
| 9,316,578 | B2 * | 4/2016 | Grier | G01N 15/1434 |
| 10,183,969 | B2 * | 1/2019 | Kyhse-Andersen | C07K 1/22 |
| 12,031,897 | B2 * | 7/2024 | Pertsinidis | G01N 15/1433 |
| 2006/0275757 | A1 * | 12/2006 | Lee | B82Y 5/00 |
| | | | | 435/7.1 |
| 2010/0044586 | A1 * | 2/2010 | Duhr | G01N 21/171 |
| | | | | 977/773 |
| 2012/0220486 | A1 * | 8/2012 | Farinas | C12Q 1/6834 |
| | | | | 436/501 |
| 2014/0065640 | A1 * | 3/2014 | Weinberger | G01N 21/45 |
| | | | | 435/7.1 |
| 2014/0152978 | A1 * | 6/2014 | Carr | G01N 15/14 |
| | | | | 356/73 |
| 2014/0227679 | A1 * | 8/2014 | Lee | B03C 1/032 |
| | | | | 435/7.1 |
| 2014/0335510 | A1 * | 11/2014 | Lukman | G01N 33/553 |
| | | | | 435/6.1 |
| 2017/0254739 | A1 * | 9/2017 | Faez | G01N 15/1484 |
| 2017/0370825 | A1 * | 12/2017 | Tatarkiewicz | G01N 15/1404 |
| 2018/0224376 | A1 * | 8/2018 | Turkcan | G01N 33/587 |
| 2019/0072472 | A1 * | 3/2019 | Clayton | G01N 15/0227 |
| 2020/0096472 | A1 * | 3/2020 | Tao | G01N 33/54353 |
| 2021/0405041 | A1 * | 12/2021 | Qin | G01N 33/54346 |
| 2022/0042978 | A1 * | 2/2022 | Gudim | G01N 33/54346 |
| 2022/0381748 | A1 * | 12/2022 | Haas | G01N 30/74 |
| 2023/0186488 | A1 * | 6/2023 | Wang | G16B 15/00 |
| | | | | 382/103 |
| 2023/0384311 | A1 * | 11/2023 | Wang | G01N 33/573 |
| 2024/0027958 | A1 * | 1/2024 | Midtvedt | G03H 1/0465 |
| 2024/0125800 | A1 * | 4/2024 | Bossmann | C12Q 1/37 |
| 2024/0288431 | A1 * | 8/2024 | Mickert | G01N 33/57415 |
| 2024/0418627 | A1 * | 12/2024 | Sandoghdar | G01N 15/1433 |
| 2025/0093633 | A1 * | 3/2025 | Kukura | G01N 15/1434 |
| 2025/0164474 | A1 * | 5/2025 | Wang | G01N 21/17 |
| 2025/0354986 | A1 * | 11/2025 | Wang | G01N 33/54313 |

OTHER PUBLICATIONS

James, Andre E. et al., "Monitoring gold nanoparticle conjugation and analysis of biomolecular binding with nanoparticle tracking analysis (NTA) and dynamic light scattering (DLS)," Analyst, 138, pp. 1212-1218. (Year: 2013).*

Jans, Hilde et al., "Dynamic Light Scattering as a Powerful Tool for Gold Nanoparticle Bioconjugation and Biomolecular Binding Studies," Analytical Chemistry, vol. 81, No. 22, pp. 9425-9432. (Year: 2009).*

Liu, Lili et al., "Particle-size Measurements in a Micro-channel with Image Dynamic Light Scattering Method," Procedia Engineering, 102, pp. 904-910. (Year: 2015).*

Ma, Guangzhong et al., "Optical imaging of single-protein size, charge, mobility, and binding," Nature Communications, 11:4768, https://doi.org/10.1038/s41467-020-18547-w, pp. 1-11. (Year: 2020).*

Ramani, Meghana et al., "Elucidating the RNA Nano-Bio Interface: Mechanisms of Anticancer Poly I:C RNA and Zinc Oxide Nanoparticle Interaction," J. Phys. Chem. C, 121, pp. 15702-15710. (Year: 2017).*

Ruseva, V. et al., "Capillary dynamic light scattering: Continuous hydrodynamic particle size from the nano to the micro-scale," Colloids and Surfaces A, 558, pp. 504-511. (Year: 2018).*

* cited by examiner

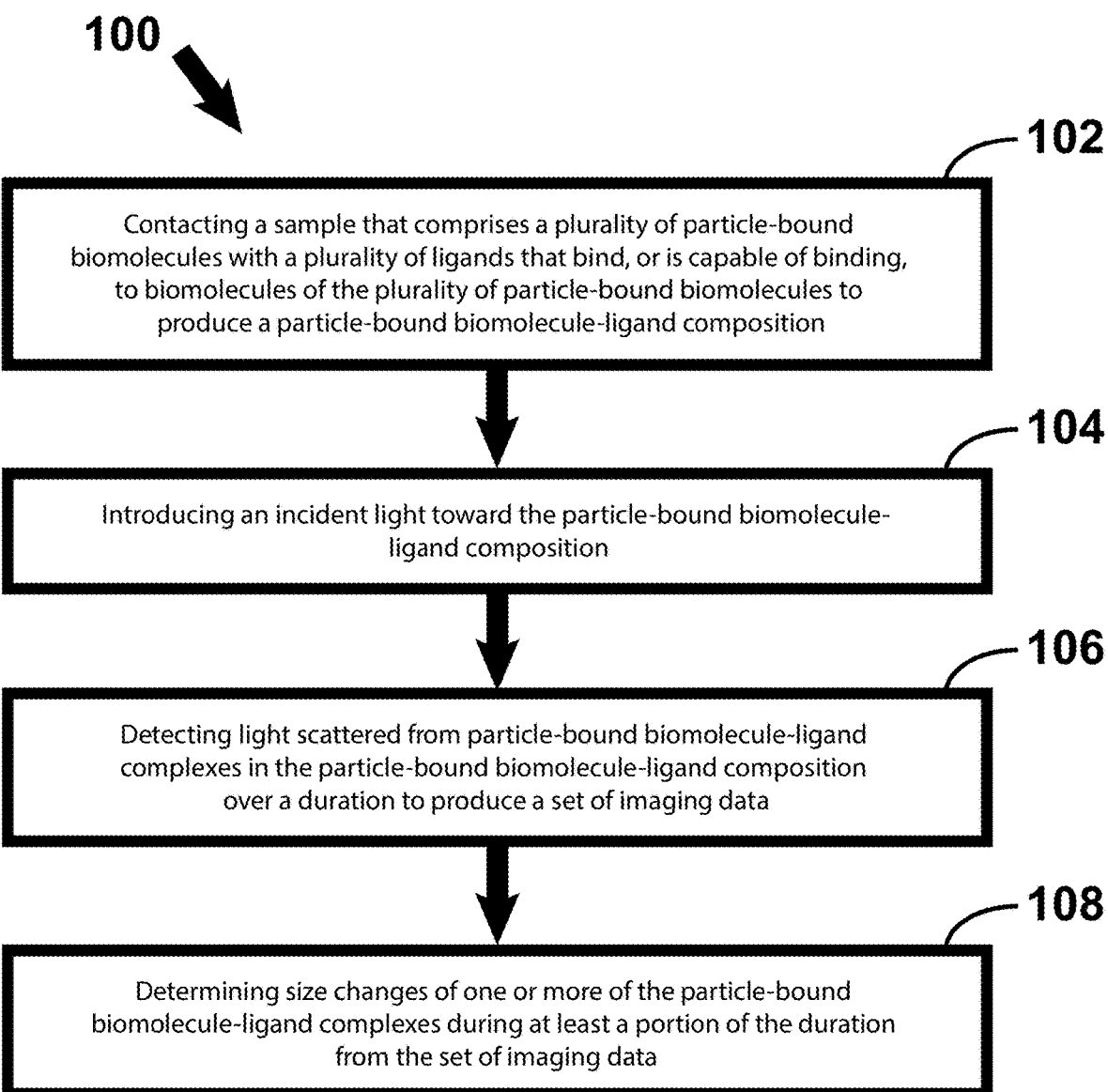

100

102

Contacting a sample that comprises a plurality of particle-bound biomolecules with a plurality of ligands that bind, or is capable of binding, to biomolecules of the plurality of particle-bound biomolecules to produce a particle-bound biomolecule-ligand composition

104

Introducing an incident light toward the particle-bound biomolecule-ligand composition

106

Detecting light scattered from particle-bound biomolecule-ligand complexes in the particle-bound biomolecule-ligand composition over a duration to produce a set of imaging data

108

Determining size changes of one or more of the particle-bound biomolecule-ligand complexes during at least a portion of the duration from the set of imaging data

FIG. 1

METHODS AND RELATED ASPECTS FOR MOLECULAR TRACKING AND ANALYSIS

CROSS-REFERENCE TO RELATED APPLICATIONS

This application claims the benefit of U.S. Provisional Application No. 63/319,208 filed Mar. 11, 2022, the disclosure of which is incorporated herein in its entirety.

BACKGROUND

Quantification of protein interaction kinetics plays an important role in the development of biosensors, discovery of disease biomarkers, understanding of biological mechanisms, and screening of drug candidates. Currently, label-free technologies including surface plasma resonance (SPR) serve as the major tool for binding kinetics analysis. However, they are still inconvenient as the binding ligands (antibodies, peptides, nucleic acids, or other molecules) need to be introduced to the functionalized sensor surface with a microfluidic system that involves careful maintenance. More importantly, purified proteins are required for the measurement, which must be immobilized onto the sensor surface with proper conjugation chemistry and blocking.

The purified proteins are often acquired by affinity separation. One example is using magnetic nanoparticles, where the target protein in a crude sample (such as cell lysate) is captured to the nanoparticle surface functionalized with affinity probes, and the bound nanoparticles can be readily pulled down by a magnetic force for separation. Finally, the captured proteins are eluted from the nanoparticles for subsequent measurements. Although using magnetic particles is simple by itself, it still introduces additional workload in terms of protein elution and buffer exchange when coupled with SPR for binding kinetics measurements. There is a need to simplify the workflow from protein purification to binding detection.

Molecules bound to the particle can increase the particle size, however, measuring such small size change (a few nm) has been challenging. Scattering based techniques like dynamic light scattering (DLS), have been used for particle size detection for over 40 years. And based on the development of modern CCD detectors and imaging techniques, nanoparticle tracking analysis (NTA) has outperformed DLS and become a better method in distinguishing aggregates and many other size related detections. Although NTA has been used for measuring molecular binding affinities, binding kinetics including association rate constant $k_a$ and dissociation rate constant $k_d$ has not been utilized.

Accordingly, there is a need for additional techniques for nanoparticle tracking analysis.

SUMMARY

This disclosure describes systems and methods for nanoparticle tracking analysis. In some embodiments, for example, the methods and related aspects of the present disclosure can be used to directly quantify binding kinetics of proteins captured on magnetic nanoparticles in solution phase. These approaches eliminate the need for eluting the proteins off the nanoparticles and subsequent immobilization to the sensing surface. These streamlined methods make protein purification and analysis simpler and faster. These and other attributes of the present disclosure will be apparent upon a complete review of the specification, including the accompanying figures.

In one aspect, the present disclosure provides a method of determining molecular binding kinetics on particles. The method includes contacting a sample that comprises a plurality of particle-bound biomolecules with a plurality of ligands that binds, or is capable of binding, to biomolecules of the plurality of particle-bound biomolecules to produce a particle-bound biomolecule-ligand composition and introducing an incident light toward the particle-bound biomolecule-ligand composition. The method also includes detecting light scattered from particle-bound biomolecule-ligand complexes in the particle-bound biomolecule-ligand composition over a duration to produce a set of imaging data, and determining size or volume changes of one or more of the particle-bound biomolecule-ligand complexes during at least a portion of the duration from the set of imaging data.

In some embodiments, the method further comprises binding the biomolecules to the particles prior to contacting the sample with the plurality of ligands. In some embodiments, the particles comprise nanoparticles. In some embodiments, the particles are magnetic. In some embodiments, the particle-bound biomolecule-ligand composition is disposed in at least one capillary. In some embodiments, the set of imaging data comprises video data. In some embodiments, the duration comprises about 15 minutes, about 10 minutes, about 5 minutes, or less time.

In some embodiments, the method includes detecting side scattered light from the particle-bound biomolecule-ligand complexes in the particle-bound biomolecule-ligand composition over the duration to produce the set of imaging data. In some embodiments, the method includes tracking positions of the one or more of the particle-bound biomolecule-ligand complexes using the set of imaging data. In some embodiments, the method includes tracking the positions of the one or more of the particle-bound biomolecule-ligand complexes in substantially real-time. In some embodiments, the method includes quantifying an amount of interaction between the plurality of particle-bound biomolecules and the plurality of ligands. In some embodiments, determining the size or volume changes of one or more of the particle-bound biomolecule-ligand complexes comprises determining hydrodynamic radii of the one or more of the particle-bound biomolecule-ligand complexes using the set of imaging data. In some embodiments, the method includes producing the set of imaging data in the absence of separating the biomolecules and/or the ligands from the particle-bound biomolecule-ligand complexes prior to or concurrent with performing the contacting, introducing, or detecting steps.

In some embodiments, the particle-bound biomolecule-ligand complexes are label-free. In some embodiments, the biomolecules and/or the ligands comprise proteins or nucleic acids. In some embodiments, the proteins comprise antibodies.

In another aspect, the present disclosure provides a system for determining molecular binding kinetics on particles. The system includes a sample container receiving area configured to receive a sample container that comprises a particle-bound biomolecule-ligand composition comprising a plurality of particle-bound biomolecules and a plurality of ligands that binds, or is capable of binding, to biomolecules of the plurality of particle-bound biomolecules, a light source configured to introduce an incident light toward the sample container receiving area, and a detector configured to collect light scattered from particle-bound biomolecule-ligand complexes in the particle-bound biomolecule-ligand composition when the sample container is received in the sample container receiving area and the incident light is introduced from the light source. The system also includes a controller that comprises, or is capable of accessing, computer readable media comprising non-transitory computer-executable instructions which, when executed by at least one electronic processor, perform at least: introducing the incident light from the light source toward the particle-bound biomolecule-ligand composition when the sample container is received in the sample container receiving area; detecting light scattered from particle-bound biomolecule-ligand complexes in the particle-bound biomolecule-ligand composition over a duration to produce a set of imaging data using the detector; and determining size or volume changes of one or more of the particle-bound biomolecule-ligand complexes during at least a portion of the duration from the set of imaging data to thereby determine the molecular binding kinetics on the particles.

In another aspect, the present disclosure provides a computer readable media comprising non-transitory computer executable instruction which, when executed by at least electronic processor, perform at least: introducing an incident light from a light source toward a sample container that comprises a particle-bound biomolecule-ligand composition comprising a plurality of particle-bound biomolecules and a plurality of ligands that binds, or is capable of binding, to biomolecules of the plurality of particle-bound biomolecules; detecting light scattered from particle-bound biomolecule-ligand complexes in the particle-bound biomolecule-ligand composition over a duration to produce a set of imaging data using the detector; and determining size or volume changes of one or more of the particle-bound biomolecule-ligand complexes during at least a portion of the duration from the set of imaging data to thereby determine the molecular binding kinetics on the particles.

In some embodiments of the systems and computer readable media disclosed herein, the sample container comprises at least one capillary. In some embodiments of the systems and computer readable media disclosed herein, the set of imaging data comprises video data. In some embodiments of the systems and computer readable media disclosed herein, the duration comprises about 15 minutes, about 10 minutes, about 5 minutes, or less time.

In some embodiments of the systems and computer readable media disclosed herein, the non-transitory computer-executable instructions which, when executed by the electronic processor, further perform at least: tracking positions of the one or more of the particle-bound biomolecule-ligand complexes using the set of imaging data. In some embodiments of the systems and computer readable media disclosed herein, the non-transitory computer-executable instructions which, when executed by the electronic processor, further perform at least: tracking the positions of the one or more of the particle-bound biomolecule-ligand complexes in substantially real-time. In some embodiments of the systems and computer readable media disclosed herein, the non-transitory computer-executable instructions which, when executed by the electronic processor, further perform at least: quantifying an amount of interaction between the plurality of particle-bound biomolecules and the plurality of ligands.

BRIEF DESCRIPTION OF DRAWINGS

FIG. 1 is a flow chart that schematically shows exemplary method steps of determining molecular binding kinetics on particles according to some aspects disclosed herein.

Figure 2:
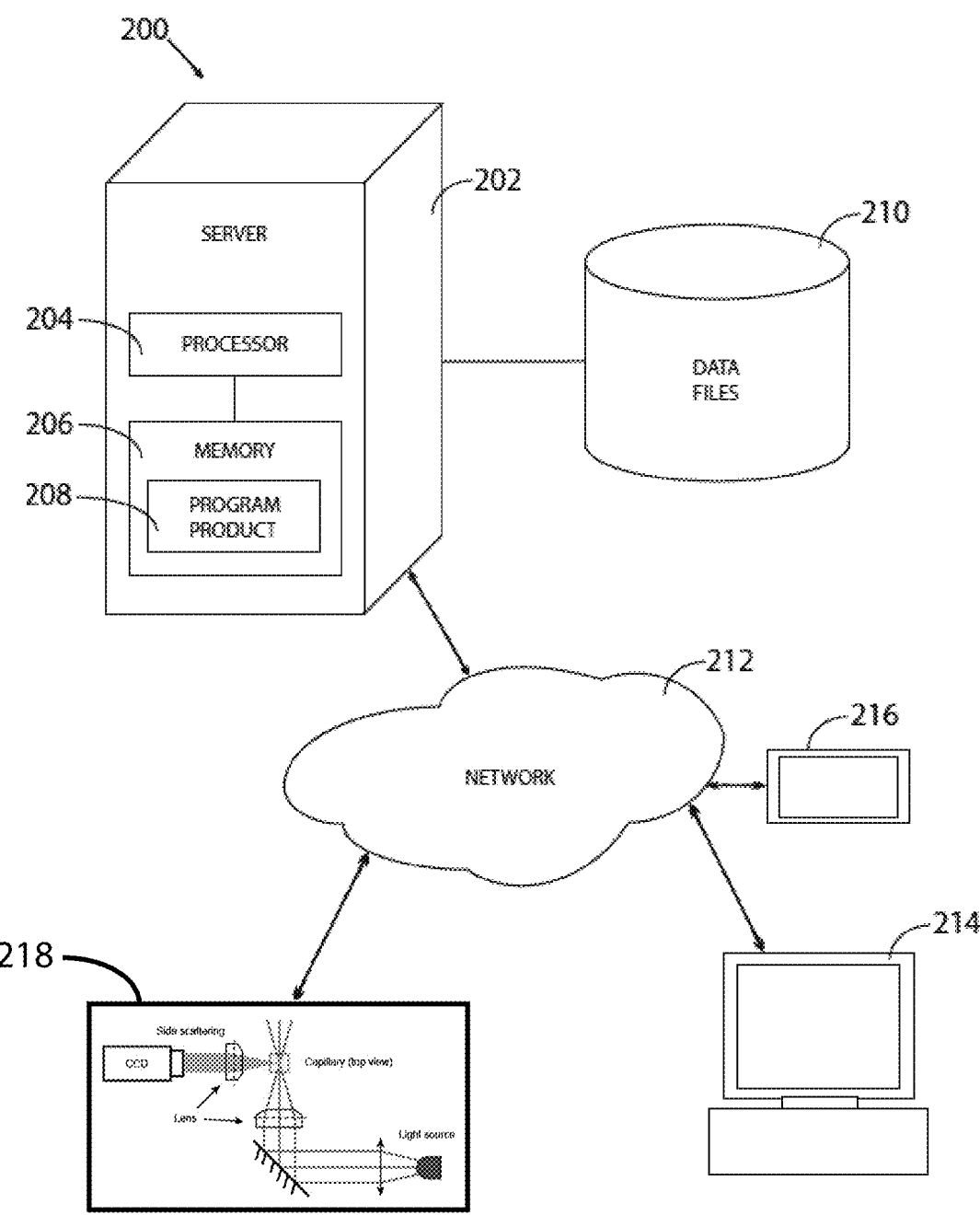
FIG. 2 is a schematic diagram of an exemplary system suitable for use with certain aspects disclosed herein.

5
DEFINITIONS

In order for the present disclosure to be more readily understood, certain terms are first defined below. Additional definitions for the following terms and other terms may be set forth throughout the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

It is also to be understood that the terminology used herein is for the purpose of describing particular embodiments only and is not intended to be limiting. Further, unless defined otherwise, all technical and scientific terms used herein have the same meaning as commonly understood by one of ordinary skill in the art to which this disclosure pertains. In describing and claiming the methods, systems, and computer readable media, the following terminology, and grammatical variants thereof, will be used in accordance with the definitions set forth below.

About: As used herein, "about" or "approximately" or "substantially" as applied to one or more values or elements of interest, refers to a value or element that is similar to a stated reference value or element. In certain embodiments, the term "about" or "approximately" or "substantially" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Antibody: As used herein, the term "antibody" refers to an immunoglobulin or an antigen-binding domain thereof. The term includes but is not limited to polyclonal, monoclonal, monospecific, polyspecific, non-specific, humanized, human, canonized, canine, felinized, feline, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. By way of example, the light chain constant region can be kappa or lambda. The term "monoclonal antibody" refers to an antibody that displays a single binding specificity and affinity for a particular target, e.g., epitope.

Biomolecule: As used herein, "biomolecule" refers to an organic molecule produced by a living organism. Exemplary biomolecules, include without limitation macromolecules, such as nucleic acids, proteins, peptides, oligomers, carbohydrates, and lipids.

Ligand: As used herein, "ligand" refers to a substance that forms a complex with another molecule, such as a biomolecule.

Nucleic Acid: As used herein, "nucleic acid" refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids can also include nucleotide analogs (e.g., bromodeoxyuridine (BrdU)), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA, cfDNA, ctDNA, or any combination thereof.

Protein: As used herein, "protein" or "polypeptide" refers to a polymer of at least two amino acids attached to one another by a peptide bond. Examples of proteins include enzymes, hormones, antibodies, and fragments thereof.

DETAILED DESCRIPTION

Pre-existing label-free techniques for quantification of protein-protein interaction often involve protein samples separated from complex media using affinity purification tools such as magnetic nanoparticles. However, the separated proteins are attached to the nanoparticles and generally need additional preparation steps, including elution and immobilization to a sensor surface before measurement. To streamline this tedious process, present disclosure provides a method, among other aspects, that can directly quantify the protein binding kinetics on nanoparticles without elution and immobilization by optically tracking the nanoparticle size change upon ligand binding. As further exemplified herein, we measured antibody binding to nanoparticles with captured protein, which was pulled down from a different medium prior to the measurement. The source of noise for the method was also analyzed. The methods and other aspects disclosed herein can simplify the workflow from protein separation to detection while providing sufficient binding kinetics and affinity information for protein studies, among other attributes.

To illustrate, FIG. 1 is a flow chart that schematically shows exemplary method steps of determining molecular binding kinetics on particles according to some aspects disclosed herein. As shown, method 100 includes contacting a sample that comprises a plurality of particle-bound biomolecules with a plurality of ligands that binds, or is capable of binding, to biomolecules of the plurality of particle-bound biomolecules to produce a particle-bound biomolecule-ligand composition (step 102) and introducing an incident light toward the particle-bound biomolecule-ligand composition (step 104). Method 100 also includes detecting light scattered from particle-bound biomolecule-ligand complexes in the particle-bound biomolecule-ligand composition over a duration to produce a set of imaging data (step 106), and determining size or volume changes of one or more of the particle-bound biomolecule-ligand complexes during at least a portion of the duration from the set of imaging data (step 108).

In some embodiments, the method further comprises binding the biomolecules to the particles prior to contacting the sample with the plurality of ligands. In some embodiments, the particles comprise nanoparticles. In some embodiments, the particles are magnetic. In some embodiments, the particle-bound biomolecule-ligand composition is disposed in at least one capillary. In some embodiments, the set of imaging data comprises video data. In some embodiments, the duration comprises about 15 minutes, about 10 minutes, about 5 minutes, or less time. In some embodiments, the particle-bound biomolecule-ligand complexes are label-free. In some embodiments, the biomolecules and/or the ligands comprise proteins or nucleic acids. In some embodiments, the proteins comprise antibodies.

In some embodiments, the method includes detecting side scattered light from the particle-bound biomolecule-ligand complexes in the particle-bound biomolecule-ligand composition over the duration to produce the set of imaging data. In some embodiments, the method includes tracking positions of the one or more of the particle-bound biomolecule-ligand complexes using the set of imaging data. In some embodiments, the method includes tracking the positions of the one or more of the particle-bound biomolecule-ligand complexes in substantially real-time. In some embodiments, the method includes quantifying an amount of interaction between the plurality of particle-bound biomolecules and the plurality of ligands. In some embodiments, determining the size or volume changes of one or more of the particle-bound biomolecule-ligand complexes comprises determining hydrodynamic radii of the one or more of the particle-bound biomolecule-ligand complexes using the set of imaging data. In some embodiments, the method includes producing the set of imaging data in the absence of separating the biomolecules and/or the ligands from the particle-bound biomolecule-ligand complexes prior to or concurrent with performing the contacting, introducing, or detecting steps.

The present disclosure also provides various systems and computer program products or machine readable media. In some aspects, for example, the methods described herein are optionally performed or facilitated at least in part using systems, distributed computing hardware and applications (e.g., cloud computing services), electronic communication networks, communication interfaces, computer program products, machine readable media, electronic storage media, software (e.g., machine-executable code or logic instructions) and/or the like. To illustrate, FIG. 2 provides a schematic diagram of an exemplary system suitable for use with implementing at least aspects of the methods disclosed in this application. As shown, system 200 includes at least one controller or computer, e.g., server 202 (e.g., a search engine server), which includes processor 204 and memory, storage device, or memory component 206, and one or more other communication devices 214, 216, (e.g., client-side computer terminals, telephones, tablets, laptops, other mobile devices, etc. (e.g., for receiving imaging data sets or results, etc.) in communication with the remote server 202, through electronic communication network 212, such as the Internet or other internetwork. Communication devices 214, 216 typically include an electronic display (e.g., an internet enabled computer or the like) in communication with, e.g., server 202 computer over network 212 in which the electronic display comprises a user interface (e.g., a graphical user interface (GUI), a web-based user interface, and/or the like) for displaying results upon implementing the methods described herein. In certain aspects, communication networks also encompass the physical transfer of data from one location to another, for example, using a hard drive, thumb drive, or other data storage mechanism. System 200 also includes program product 208 (e.g., for tracking molecular binding kinetics on particles as described herein) stored on a computer or machine readable medium, such as, for example, one or more of various types of memory, such as memory 206 of server 202, that is readable by the server 202, to facilitate, for example, a guided search application or other executable by one or more other communication devices, such as 214 (schematically shown as a desktop or personal computer). In some aspects, system 200 optionally also includes at least one database server, such as, for example, server 210 associated with an online website having data stored thereon (e.g., entries corresponding to molecular interaction data, etc.) searchable either directly or through search engine server 202. System 200 optionally also includes one or more other servers positioned remotely from server 202, each of which are optionally associated with one or more database servers 210 located remotely or located local to each of the other servers. The other servers can beneficially provide service to geographically remote users and enhance geographically distributed operations.

As understood by those of ordinary skill in the art, memory 206 of the server 202 optionally includes volatile and/or nonvolatile memory including, for example, RAM, ROM, and magnetic or optical disks, among others. It is also understood by those of ordinary skill in the art that although illustrated as a single server, the illustrated configuration of server 202 is given only by way of example and that other types of servers or computers configured according to various other methodologies or architectures can also be used. Server 202 shown schematically in FIG. 2, represents a server or server cluster or server farm and is not limited to any individual physical server. The server site may be deployed as a server farm or server cluster managed by a server hosting provider. The number of servers and their architecture and configuration may be increased based on usage, demand and capacity requirements for the system 200. As also understood by those of ordinary skill in the art, other user communication devices 214, 216 in these aspects, for example, can be a laptop, desktop, tablet, personal digital assistant (PDA), cell phone, server, or other types of computers. As known and understood by those of ordinary skill in the art, network 212 can include an internet, intranet, a telecommunication network, an extranet, or world wide web of a plurality of computers/servers in communication with one or more other computers through a communication network, and/or portions of a local or other area network.

As further understood by those of ordinary skill in the art, exemplary program product or machine readable medium 208 is optionally in the form of microcode, programs, cloud computing format, routines, and/or symbolic languages that provide one or more sets of ordered operations that control the functioning of the hardware and direct its operation. Program product 208, according to an exemplary aspect, also need not reside in its entirety in volatile memory, but can be selectively loaded, as necessary, according to various methodologies as known and understood by those of ordinary skill in the art.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 208 implementing the functionality or processes of various aspects of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Program product 208 is optionally copied from the computer-readable medium to a hard disk or a similar intermediate storage medium. When program product 208, or portions thereof, are to be run, it is optionally loaded from their distribution medium, their intermediate storage medium, or the like into the execution memory of one or more computers, configuring the computer(s) to act in accordance with the functionality or method of various aspects disclosed herein. All such operations are well known to those of ordinary skill in the art of, for example, computer systems.

In some aspects, program product 208 includes non-transitory computer-executable instructions which, when executed by electronic processor 204, perform at least: introducing an incident light from a light source toward a sample container that comprises a particle-bound biomolecule-ligand composition comprising a plurality of particle-bound biomolecules and a plurality of ligands that binds, or is capable of binding, to biomolecules of the plurality of particle-bound biomolecules; detecting light scattered from particle-bound biomolecule-ligand complexes in the particle-bound biomolecule-ligand composition over a duration to produce a set of imaging data using the detector; and determining size or volume changes of one or more of the particle-bound biomolecule-ligand complexes during at least a portion of the duration from the set of imaging data to thereby determine the molecular binding kinetics on the particles.

Typically, imaging is obtained using device 218. As shown, device 218 includes a sample container receiving area configured to receive a sample container (e.g., a capillary tube or the like) that comprises a particle-bound biomolecule-ligand composition comprising a plurality of particle-bound biomolecules and a plurality of ligands that binds, or is capable of binding, to biomolecules of the plurality of particle-bound biomolecules, a light source configured to introduce an incident light toward the sample container receiving area, and a detector (shown as a CCD camera) configured to collect light scattered from particle-bound biomolecule-ligand complexes in the particle-bound biomolecule-ligand composition when the sample container is received in the sample container receiving area and the incident light is introduced from the light source.

Example: Magnetic Nanoparticle Tracking for One-Step Protein Separation and Binding Kinetics Analysis

Methods

Materials

Bovine serum albumin (BSA) coated $Fe_3O_4$ magnetic nanoparticles were purchased from Nanopartz (AM1-70-BSA-DIH-2.5-1 and A1M1-100-BSA-DIH-2.5-1). Nanoparticles with diameter of 70 nm and 100 nm were used for anti-BSA binding experiment and secondary antibody binding experiment, respectively. BSA antibody (anti-BSA) produced in rabbit was purchased from Sigma-Aldrich. Goat anti-rabbit IgG (secondary antibody) was purchased from Abcam (ab182016). All proteins were diluted to appropriate concentrations for measurement in 1× phosphate buffered saline (PBS). For SPR measurements, the gold coated sensor chips (47 nm Au film on cover glass) were fabricated by e-beam evaporation. SH-PEG8-COOH), N-hydroxysulfosuccinimide sodium salt (NHS), and N-(3-dimethylaminopropyl)-N'-ethylcarbodiimide hydrochloride (EDC) were purchased from Sigma-Aldrich. MT(PEG)4 was purchased from Thermo Fisher Scientific.

Experimental Setup

The light source used in the experimental system was a multimode blue laser with a center wavelength at 450 nm and output power set at 400 mW (L450P1600MM, Thorlabs). The light was collimated with an aspheric lens and focused on the sample with a 20× long working distance objective. The sample solution was trapped in a square glass capillary with an inner width of 1 mm and wall thickness of 0.2 mm (VitroTubes, 8100). A 10× zoom lens (VZM™ 1000, Edmund Optics) and a CCD camera (Pike F032B, Allied Vision) were used to collect the side scattered light from the sample, with a camera frame rate of 60 frames per second (fps). SPR measurements were performed on SPRm 200 with an autosampler (Biosensing Instrument).

Protein Binding Measurements

The binding between anti-BSA and BSA coated nanoparticles were measured in both end-point and real-time fashions. For the end-point measurements, different concentrations of anti-BSA were mixed with BSA coated magnetic nanoparticles (33 pM) and incubated for 30 min to reach the equilibrium. Then 25 μL of the mixture solution was loaded into the capillary and sit for 5 min to minimize particle flows inside the capillary caused by sample loading. A video was recorded for 5 min at 60 fps. For real-time measurements, the anti-BSA and the BSA coated particles were mixed and immediately loaded into the capillary. A video was taken after 90 s for 13 min at 60 fps. Both measurements were repeated independently for 10 times so that the total particle numbers are sufficient for statistical analysis.

The binding between secondary antibody and primary antibody (anti-BSA captured on BSA coated nanoparticles) was measured in real-time. Excess amount (233 nM) of primary antibody (anti-BSA) was incubated with 10 times diluted BSA coated magnetic nanoparticles for at least 30 min to reach equilibrium. Then the primary antibody captured nanoparticles were pulled down by a magnet and the supernatant was discarded. The nanoparticles were resuspended and diluted 50 times with PBS and mixed with secondary antibody at different concentrations. The mixture was immediately transferred to the capillary and imaged at 15 fps for 10 min. Note that the time interval between mixing and imaging was kept at 180 s for consistency. The measurement was repeated for 3 times.

For SPR measurement, firstly, the gold chips were soaked in 0.2 mM SH-PEG8-COOH) and 0.2 mM MT(PEG)4 overnight to form a COOH functionalized surface. Then the surface was activated with 50 mM NHS and 200 mM EDC for 20 min, followed by incubating with 1 mg/mL BSA (for anti-BSA binding measurement) or 50 nM anti-BSA (for secondary antibody binding measurement) for 30 min. Finally, the remaining active sites were quenched with 20 mM ethanolamine for 5 min and the chip was washed with PBS.

Data Analysis

Figure 5A:
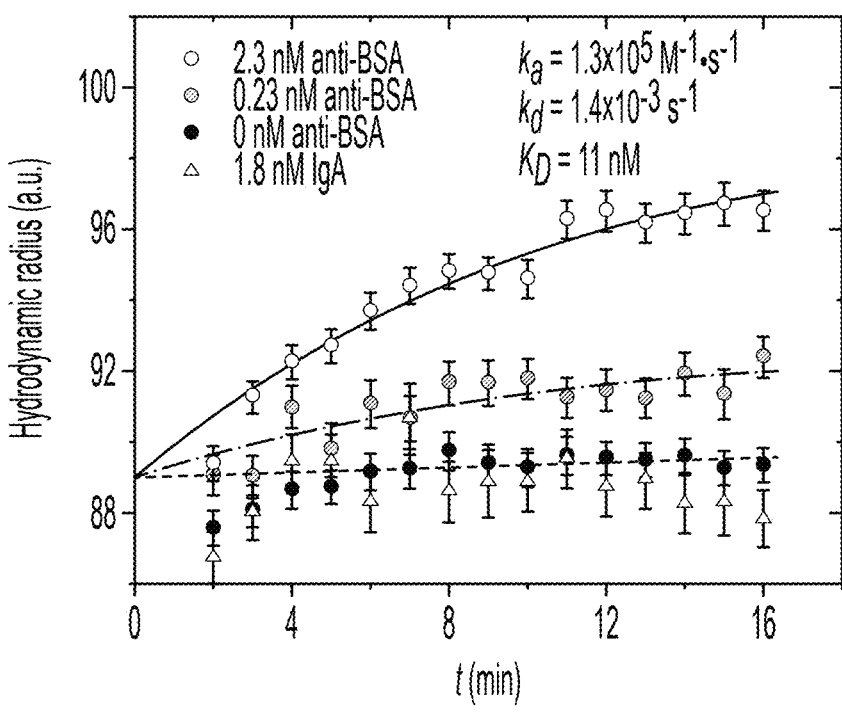
FIGS. 5A-5B. Measuring the binding kinetics between BSA and anti-BSA via particle size tracking. (a) Time-resolved diameter change at different anti-BSA concentrations reveals the binding kinetics. The dashed lines are fitting of the data to Eq. 3. The error bars are standard deviation of >2000 particles. (b) BSA and anti-BSA measured by SPR, where the dashed curve is fitting of the data.

Particle displacements in each frame were extracted from the recorded video using the TrackMate plugin in ImageJ software. The tracking results were further processed with MATLAB 2019a to filter out short tracking paths and obtain the histogram for size analysis. Tracks shorter than 50 frames were excluded from the data. To extract binding kinetics, the raw video (15 min long) was divided into 15 segments, with 1 min for each, and the particle size change within each segment was measured to obtain the time-resolved size change plot (FIG. 5A). Due to the limited number of particles within the field of view (500 particles), 10 replicates were measured for each concentration, and the results were combined such that sufficient data points could be used to generate the histogram with desired accuracy. The SPR results were fitted with ImageAnalysis Version 1.8.0.5 (Biosensing Instrument) and Scrubber 2.0. Other fittings and Monte Carlo simulation were performed with MATLAB 2019a.

We note that it is not necessary to derive the absolute value of particle radius or volume using Eq. 1 for ligand binding kinetics analysis, because r is proportional to $$\frac{t}{\bar{x}^2}.$$

Figure 4A:
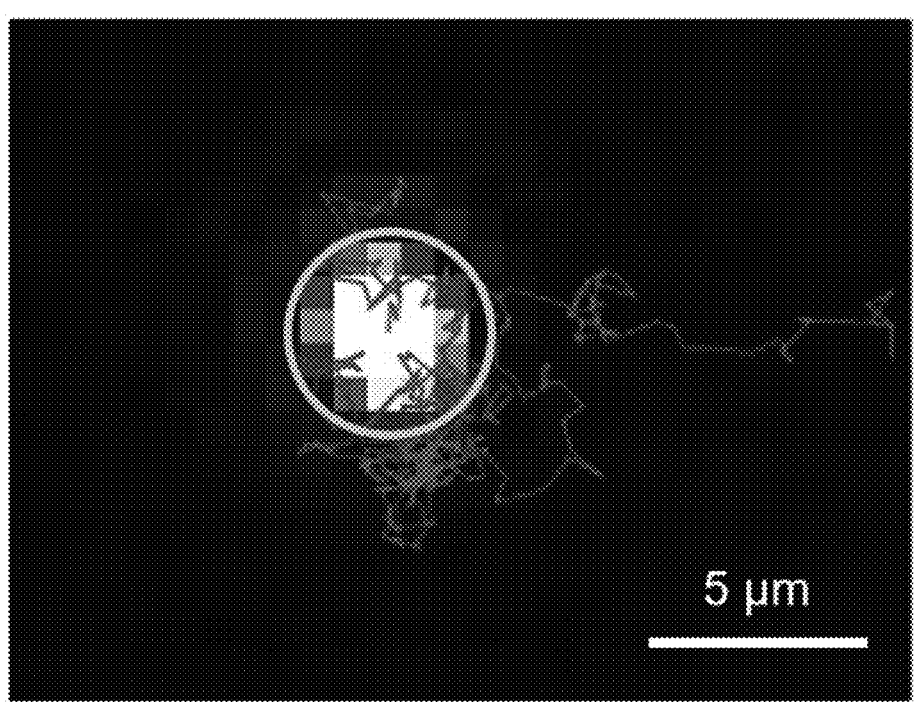
FIGS. 4A-4D. Measuring particle size and ligand binding affinity. (a) Tracking the motion of a single particle. The bright spot in the circle is the particle, and its motion within 5.2 s is tracked (grey trace). (b) Histogram showing the diameter distribution obtained from the track of >2000 particles. (c) Anti-BSA is added to BSA coated particles, and the binding increases the particle size. (d) Hydrodynamic diameter of the particles as a function of anti-BSA concentration at equilibrium. The inset shows plotting the data in log-log scale, where the dotted curve is fitting of the data to Eq. 2. The error bars represent standard deviation of >2000 individual particles.
Figure 4B:
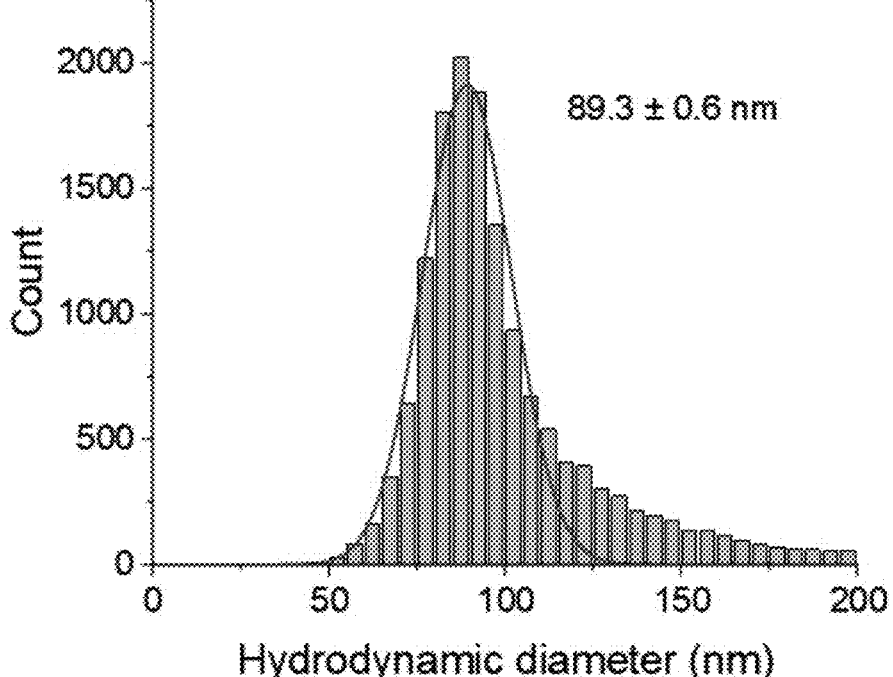
Figure 4C:
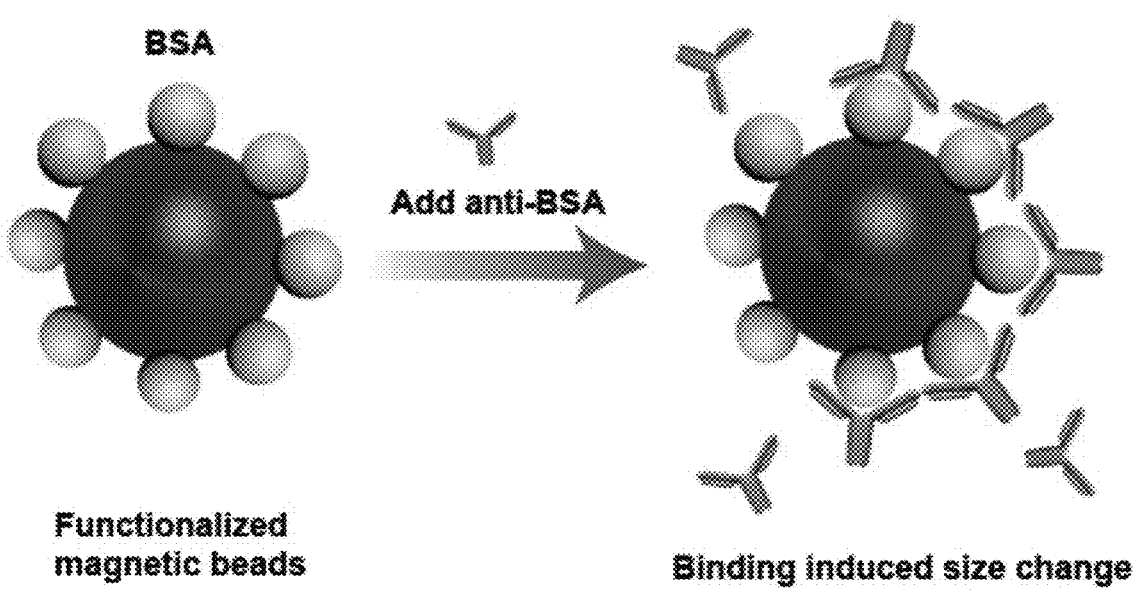

Thus, we can use r'=kr to represent the radius or $V'=k^3V$ to represent the volume, both in arbitrary unit. k is a function of T and η, but can be treated as a constant if we assume T and η do not change during measurement. In FIG. 4B, we calculated the absolute diameter by assuming T=300 K and η=8.3×10$^{-4}$ Pa·s. For the other figures, we use arbitrary unit for convenience.

Results

Detection Principle

Figure 3A:
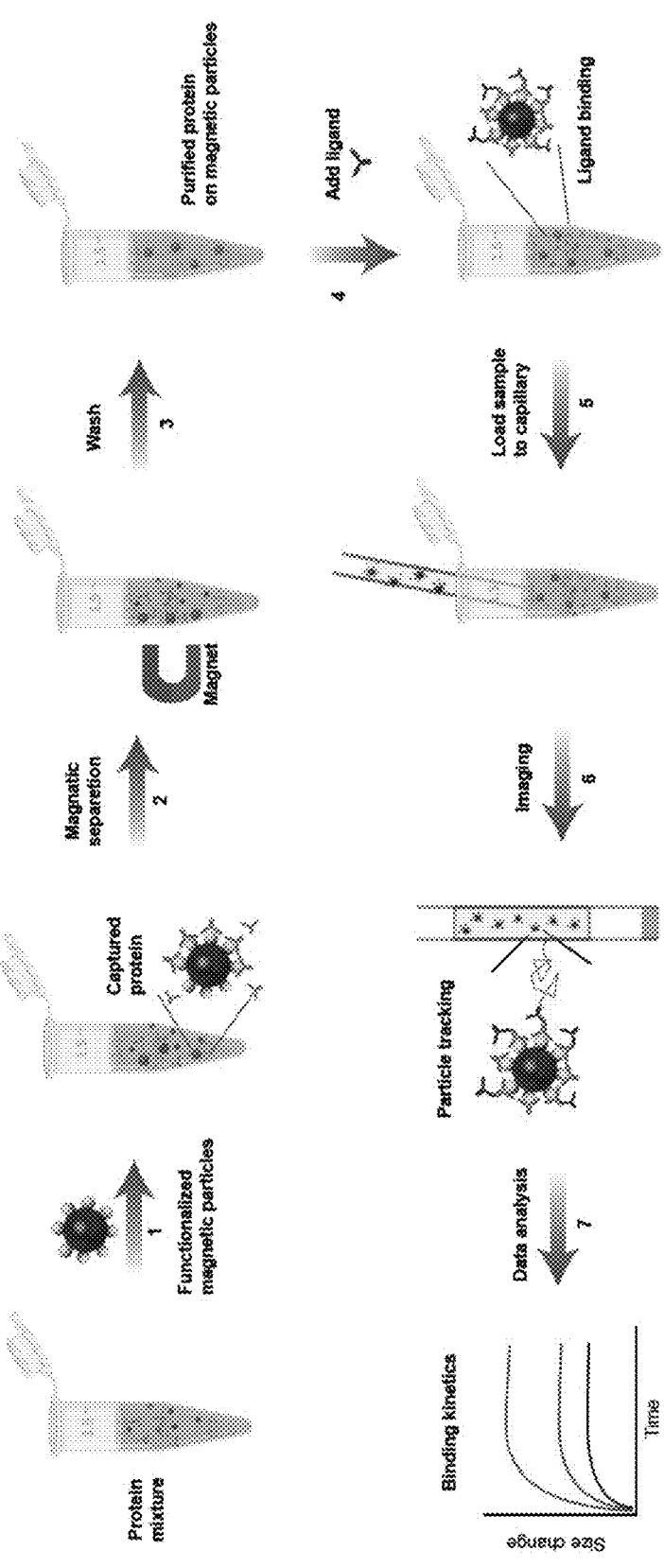
FIGS. 3A-3C. Detection principle. (a) Protocols showing capture of protein to the magnetic particles (steps 1-3) and the subsequent ligand binding detection (steps 4-7). After adding ligand (step 4), a small volume of the mixture was immediately transferred to a capillary, which was mounted on the imaging setup for particle motion tracking. (b) Optical setup for particle tracking. The incident light is focused on the capillary and side scattered light of particles are imaged. (c) A zoom-in of the capillary showing the region being imaged (left) and an image showing the scattering light of the particles (middle). The particles are tracked, and the hydrodynamic radius is extracted from thousands of particles (right).
Figure 3B:
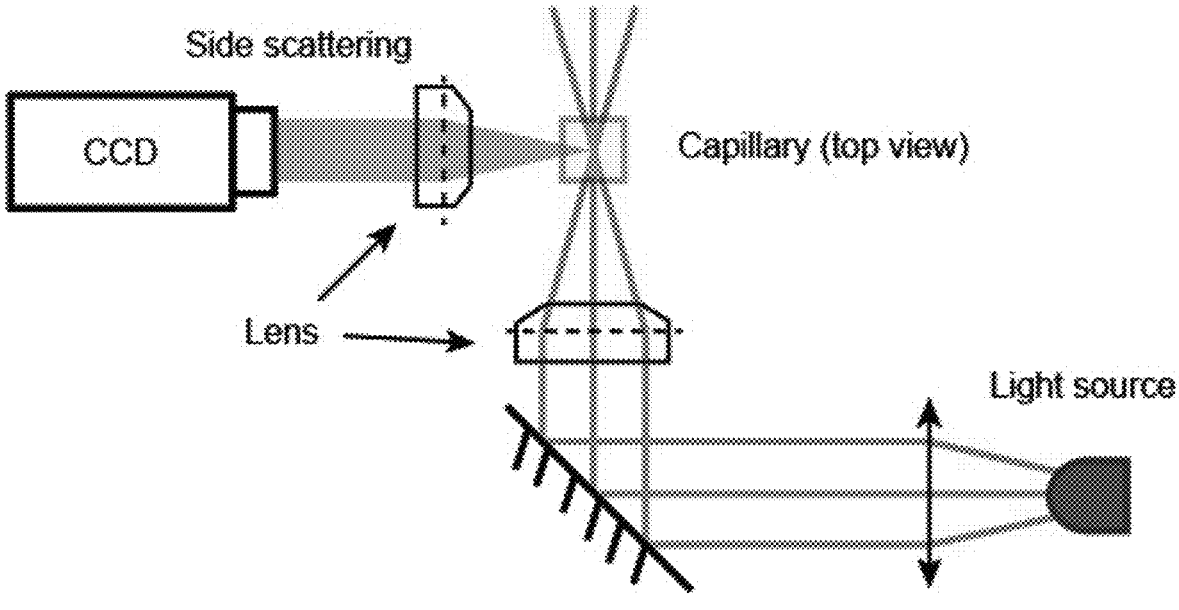
Figure 3C:
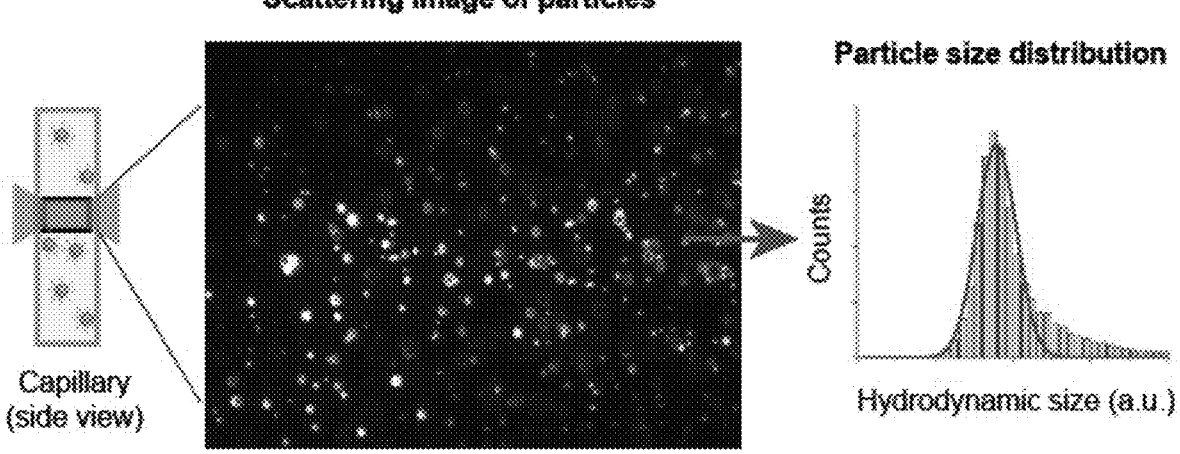

After capturing the molecules of interest, the magnetic nanoparticles were separated from the original solution and resuspended in PBS buffer. Then a small portion of the nanoparticle solution was transferred to a square-walled glass capillary, which was mounted on the optical detection setup (FIG. 3B). An incident light was focused on the capillary to illuminate the nanoparticles. The scattered light from the nanoparticles were collected at normal direction by a CCD camera as dark field images. The motion of each individual nanoparticle can be described by the Einstein-Smoluchowski equation as $$\frac{\bar{x}^2}{2t} = D,$$

where $\bar{x}^2$ is the mean square displacement (MSD) over time (t) and D is the diffusion coefficient, which is a function of buffer viscosity (η), temperature (T) and hydrodynamic radius of the nanoparticles (r), given by $$D = \frac{k_B T}{6\pi\eta r},$$

where $k_B$ is Boltzmann's constant. Therefore, for given viscosity and temperature, the size of the nanoparticle is merely dependent on its displacement over time:

$$r = \frac{k_B T}{3\pi n} \cdot \frac{t}{\bar{x}^2} \tag{1}$$

This quantitative relationship allows us to measure the particle size or volume ($V=4/3\pi r^3$) by tracking its displacement over time.

When ligand binds to the target protein on the nanoparticle, the volume is changed, therefore it is possible to extract ligand binding kinetics by analyzing particle volume change ($\Delta V$). The binding kinetic constants includes association rate constant ($k_a$), dissociation rate constant ($k_d$), and dissociation constant or binding affinity ($K_D$), where $K_D=k_d/k_a$. $K_D$ is a measure of equilibrium and can be determined from the sensor response by $$R_{eq} = \frac{c}{c + K_D} R_{max},$$

where c is the ligand concentration, and $R_{eq}$ and $R_{max}$ are the response at equilibrium and maximum response when all the binding sites on the surface are completely occupied by the ligand, respectively. Since the ligands on the particle surface increase its volume, the volume change at equilibrium ($\Delta V_{eq}$) can be described by $$\Delta V_{eq} = A \cdot \frac{c}{c + K_D} R_{max}, \tag{2}$$

where A is a constant. Eq. 2 allows us to determine $K_D$ by measuring $\Delta V_{eq}$ at different ligand concentrations in an end-point fashion. To obtain $k_a$ and $k_d$, $\Delta V$ should be continuously measured before the equilibrium. At time t, $\Delta V$ is given by, $$\Delta V_t = \Delta V_{eq}\left[1 - e^{-(k_a c + k_d)t}\right]. \tag{3}$$

Since $\Delta V_{eq}$ is known from Eq. 2, we can extract $k_a$ and $k_d$ by fitting the time dependent volume change with Eq. 3.

Measuring Binding Induced Size Change and Binding Affinity

To validate our theory and demonstrate particle size measurement via tracking the Brownian motion, we suspended 70 nm BSA coated magnetic nanoparticles in PBS and recorded the Brownian motion over time. FIG. 4A shows a representative track of an individual particle in 5.2 s at a temporal resolution of 16.7 ms. The average displacement of the particle is 9.75 µm/s, corresponding to 90 nm in size according to Eq. 1, close to the size of 70 nm particle with a layer of BSA (which is ~8 nm, so the diameter is 70±8×2 nm). Due to the limited depth of field of our imaging setup, a single particle is estimated to move out of the view in less than 2 min, which does not provide sufficient accuracy for size measurement. Therefore, we tracked multiple nanoparticles in the sample solution and generated a histogram to determine the particle size (FIG. 4B). The histogram obtained from over 2000 nanoparticles tracked in 10 independent experiments shows an average particle size of 89 nm, which agrees with the size from the manufacture (82 nm).

Figure 4D:
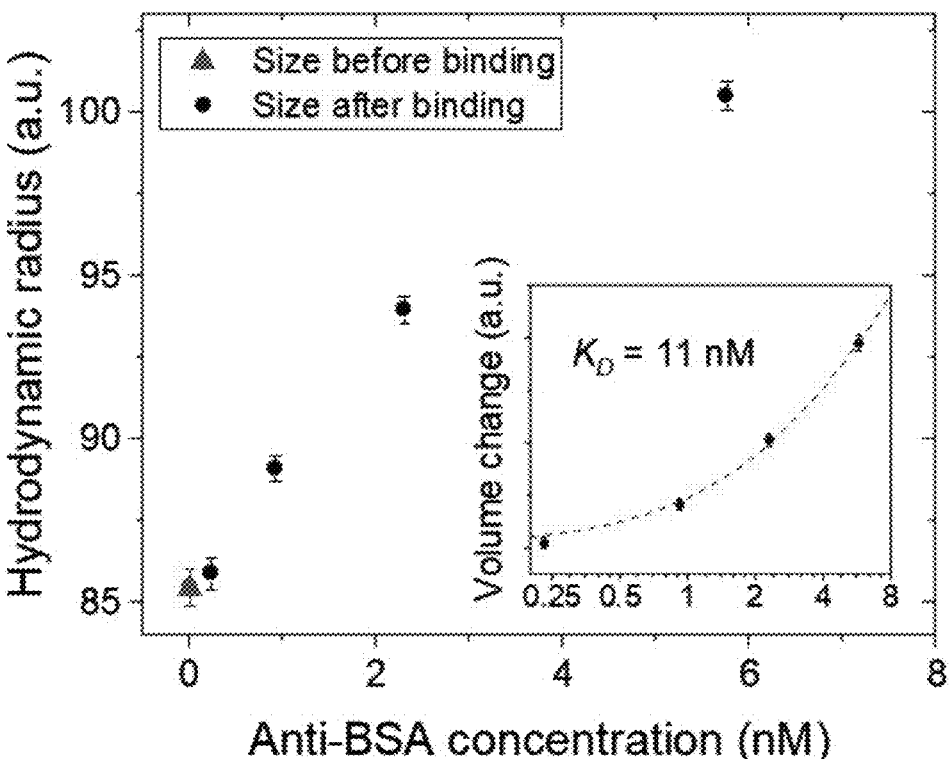

Next, we measured the particle size change due to protein binding. We mixed the BSA coated nanoparticles with anti-BSA antibody at different concentrations and incubated the mixture for 30 min to allow the interaction to reach equilibrium. Then the particles were transferred to the capillary for imaging. We found that the average volume of the nanoparticles increased and was dependent on anti-BSA concentration (FIG. 4D). By fitting the data with Eq. 2, $K_D$ was determined to be 11 nM (FIG. 4D), which was consistent with that obtained by SPR (see below). Note that arbitrary unit is used to present hydrodynamic radius or volume in this work for convenience (see Methods), because the binding kinetics is determined by the relative change of the radius or volume, not their absolute values.

Binding Kinetics Between BSA and Anti-BSA

Figure 5B:
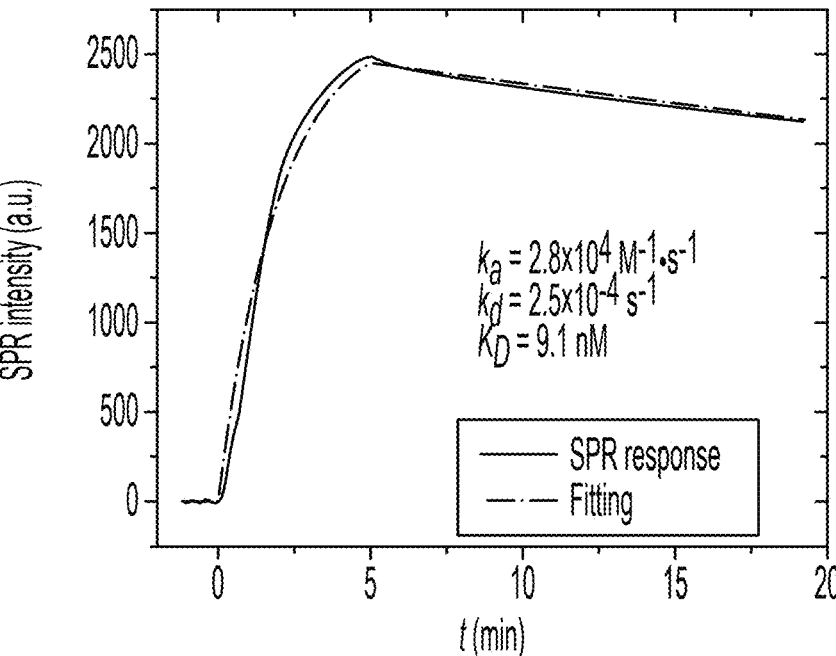

The above end-point analysis only measures the equilibrium state, which does not provide kinetic information. To measure $k_a$ and $k_d$, we recorded particle volume change in every 1 min before reaching the equilibrium and fitted the data to Eq. 3 (FIG. 5A). $k_a$ and $k_d$ were determined to be $1.3 \times 10^5$ $M^{-1} \cdot s^{-1}$ and $1.4 \times 10^{-3}$ $s^{-1}$, respectively. To confirm the volume change was due to specific binding between BSA and anti-BSA, we used IgA instead of anti-BSA and performed the same measurement. IgA could not bind to BSA, and as expected, we did not observe volume change of the BSA coated nanoparticles (FIG. 5A). To validate the result, we used SPR to quantify the binding kinetics between BSA and anti-BSA, where BSA was immobilized on the sensor surface and anti-BSA was flowed over the surface. The results were $k_a = 2.8 \times 10^4$ $M^{-1} \cdot s^{-1}$, $k_d = 2.5 \times 10^{-4}$ $s^{-1}$ and $K_D = 9.1$ nM (FIG. 5B). Although $K_D$ was consistent with our result, $k_a$ and $k_d$ were ~5 times smaller. The difference in rate constants might be due to the different surface chemistry between the magnetic particles and the gold SPR sensor chip.

Affinity Purification and Direct Binding Kinetics Analysis

Figure 6A:
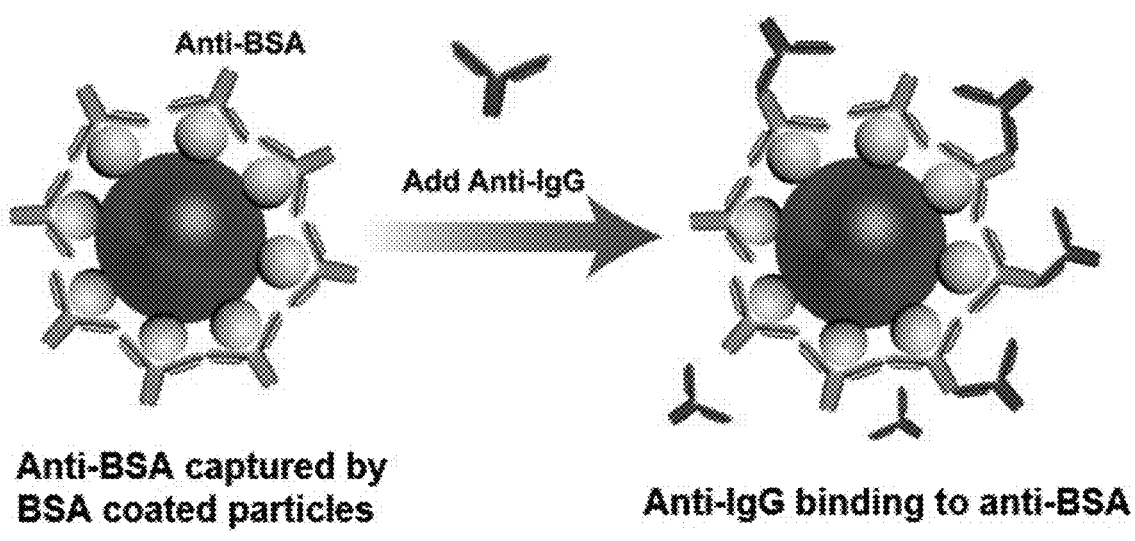
FIGS. 6A-6D. Secondary antibody binding to captured primary antibody. (a) Anti-BSA (primary antibody) captured by BSA particles are used to measure the binding kinetics between anti-BSA and anti-IgG (secondary antibody). (b) The size change vs. anti-IgG concentration at equilibrium. The inset shows plotting the data in logarithmic scale and fitting to Eq. 2. (c) Particles with anti-BSA captured were mixed with different concentrations of anti-IgG, and the size change was monitored over time. The error bars in b and c represent standard deviation obtained from >2000 particles. (d) SPR measurement of anti-IgG binding to surface immobilized anti-BSA. The dashed curve is fitting of the data.
Figure 6B:
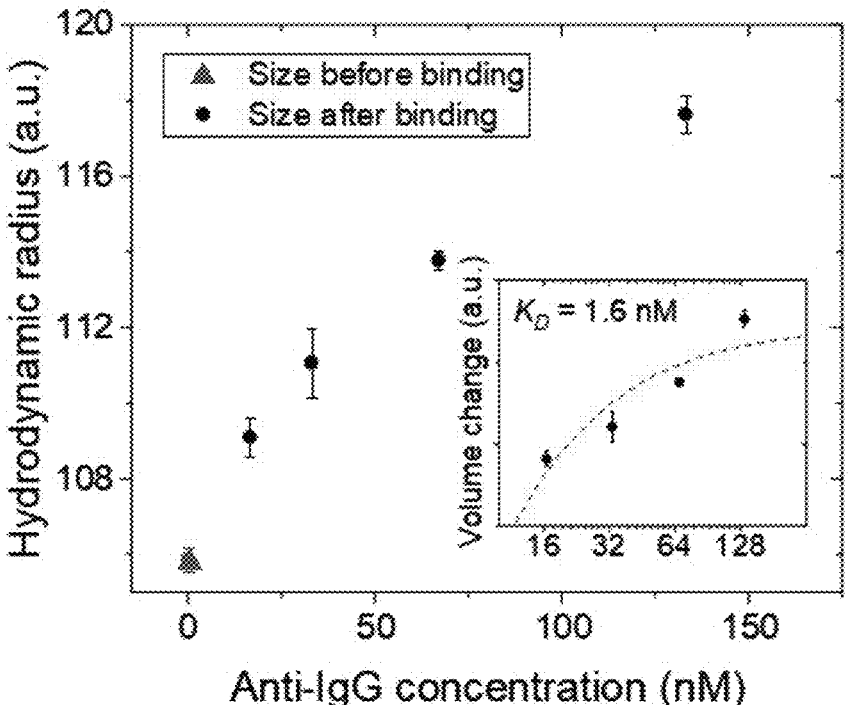
Figure 6C:
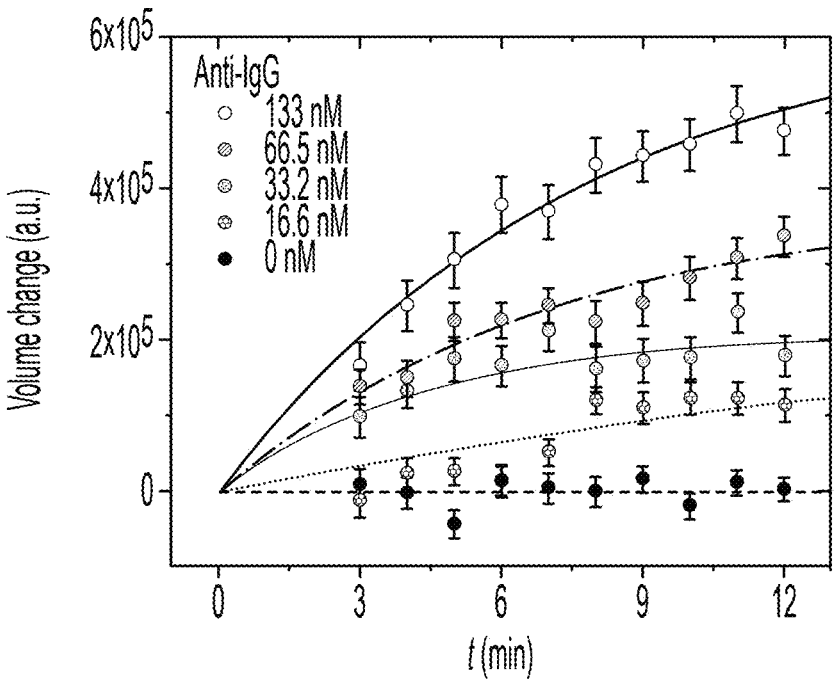
Figure 6D:
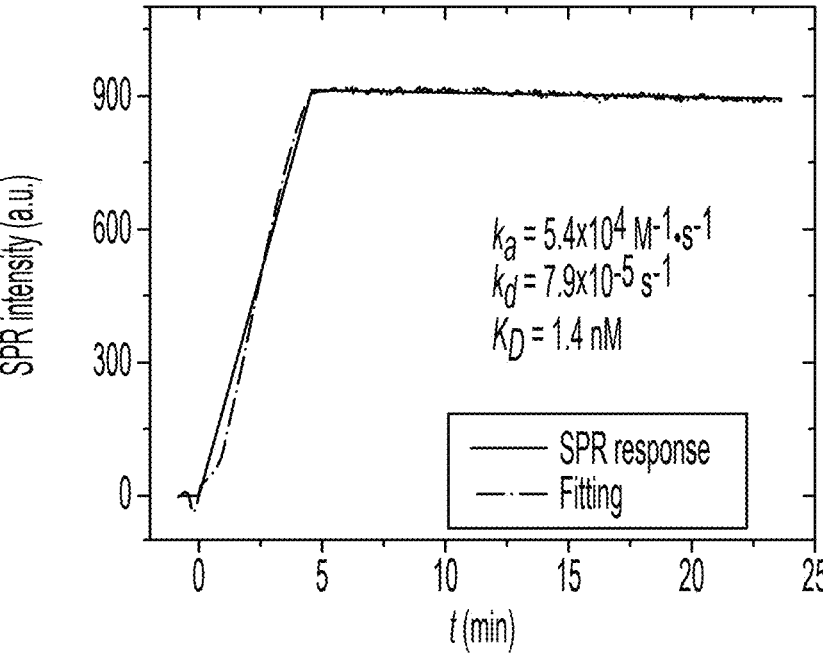

The functionalized magnetic nanoparticles allow us to specifically separate a protein of interest from the original medium and measure its binding kinetics with a ligand directly on the particles. To demonstrate this capability, we first added BSA coated nanoparticles to 233 nM anti-BSA solution. Anti-BSA were specifically bound to the nanoparticles, however, the excess amount of anti-BSA remaining in the solution would affect the interaction between the particle captured anti-BSA and its ligand. We exchanged the anti-BSA solution to PBS buffer by using a magnet (FIG. 3A). Next, we used a secondary antibody to bind the captured anti-BSA (FIG. 6A) by introducing different concentrations of the secondary antibody directly to the nanoparticles and recorded the particle size change over time (FIG. 6B). We first fitted the response curve at equilibrium state for different concentrations to Eq. 2 and obtained the $K_D = 1.6$ nM. With given $K_D$, the time-resolved response curves were fitted to Eq. 3 and the average kinetic constants, $k_a$ and $k_d$ were determined to be $4.4 \times 10^4$ $M^{-1} \cdot s^{-1}$ and $7.1 \times 10^{-5}$ $s^{-1}$, respectively (FIG. 6C). To validate our result, we performed SPR measurement by immobilizing anti-BSA on the sensor surface and flowing 133 nM anti-IgG over the surface (FIG. 6D). The kinetic constants were $k_a = 5.4 \times 10^4$ $M^{-1} \cdot s^{-1}$, $k_d = 7.9 \times 10^{-5}$ $s^{-1}$ and $K_D = 1.4$ nM, agree with the particle tracking result. The mass transfer rate constant was fitted to be $k_m = 3.1 \times 10^7$ $M^{-1} \cdot s^{-1}$, which was much greater than $k_a$, suggesting the interaction was not mass transport limited.

Discussions

Noise Analysis

The particle size obtained from a single measurement presents a broad distribution (FIG. 4B), which affects the precision and accuracy. The distribution was fitted to Gaussian with mean value r and standard deviation σ. For each single measurement using the same sample, r and σ were slightly different. Below, we investigate possibilities that could cause broadening of the peak and the variation between measurements.

Since the Brownian motion is a random process, intrinsic statistical error would arise from sampling. To determine the appropriate sample size for our measurement, we performed a Monte Carlo simulation. To simplify the model, we assume the Brownian motion takes place in one dimension. We note that reducing the dimension does not lose information for the Brownian motion, as it is statistically equivalent in each dimension. We studied four important parameters in our simulation: particle size distribution, tracking duration distribution, the number of tracks obtained from each particle, and particle number. In the simulation, we start with the simplest scenario, and then gradually include additional parameters to mimic the experimental condition, and finally compare the tracking results. We set up four cases as the following:

(1) All particles (particle number=500) have the same size (50 nm) and tracking duration (50 frames), and each particle generates only one track.

(2) Additional to (1), the particle size is uniformly distributed within 45-55 nm.

(3) Additional to (2), the tracking duration is considered, with an exponential distribution with μ (decay constant) set at 120 frames (note that tracks shorter than 50 frames or longer than 900 frames were removed.

(4) Additional to (3), multiple tracks generated from each particle is considered.

We performed simulations for each case for 1000 times to study the difference. The mean value of r and standard deviation σ in each case were determined. We also increased the particle number to 5000 and performed the simulation again. The results indicate that the particle number (case 1) and track duration (case 3) are main factors that influence the accuracy and precision. Sufficient number of tracks reduce the variance and thus improves precision (when particle number reaches 5000, the variance is much smaller than our experimental value), while longer tracking time reduces the fitting error and improves accuracy. In contrast, the size distribution (case 2) and multiple tracks from the same particle (case 4) can be neglected under our experimental conditions (size distribution is ±10 nm and each particle generates <10 tracks), especially when particle number is sufficient (e.g., 5000). In fact, increasing particle counting number (case 1) is the most practical way to improve the detection accuracy, because tracking duration (case 3) is limited by the field of depth of our optical setup.

The second noise source that needs to be considered is false track from impurities and aggregates, which dramatically influence the fitting quality. In addition, the interference patterns from these aggregates and surrounding particles are also tracked. These false tracks, which although generate inaccurate size information, can be readily distinguished as they show blinking image intensities and short tracking durations. To reduce the false tracks in data processing, we applied a filter to block tracks with duration <3 s. The experimental fitting error can be reduced ~4 times due to narrowing down the distribution. Further increasing the duration threshold can achieve better accuracy, but more replicates should be measured to maintain sufficient particle counts and hence the precision. Besides, higher sample quality with less aggregates and using nanoparticles with stronger scattering intensity can improve detection accuracy and precision.

The third noise source is laser heating induced flow in the solution, which leads to particle drifting. As a result, the MSD contains information from both Brownian motion and drift. The drift will increase the value of MSD and reduce the measured hydrodynamic size. In addition, according to Eq. 1, because MSD is a function of temperature, high temperature can increase MSD by itself, and thus further reduces the measured hydrodynamic size. Our experiment results show particle size increases in the first few minutes (FIG. 5A), which indicates that the drift dominates in the beginning due to the sample handling.

Sample and Particle Concentrations

Our method can quantify antibody binding kinetics at concentrations from sub-nM to hundreds of nM (FIGS. 5A and 6C), which covers the typical concentration range in immunoassays. The upper limit of dynamic range is due to the particle concentration because the scattering of different particles interferes and leads to false tracking. The particle concentration suitable for the current setup is below $10^{-14}$ M. Considering the particle size and the number of protein molecules captured on each particle, the maximum protein (ligand) concentration is $\sim 10^{-5}$ M. The lower limit is decided by the size of molecule and binding affinity. Larger size and higher affinity would lead to a lower limit smaller than the 0.23 nM we measured using antibody.

Binding Kinetics Vs Dynamic Range

In our measurement, the particles are first mixed with the ligand in a centrifuge tube and then loaded into a capillary (FIG. 3A), which takes ~2 min including sample mixing and settling down after loading. As a result, fast binding process finished within 2 min cannot be resolved. In other words, if the binding process reaches equilibrium within the 2 min, the kinetics curves cannot be accurately fitted by Eq. 3 to extract the binding kinetic constants. One way to mitigate this issue is to use lower sample concentration such that the equilibrium occurs beyond the 2 min. However, low concentrations reduce the magnitude of signal, and the signal will not be detectable if it is below the noise level. There is a tradeoff between binding kinetics and dynamic range.

Figure 7A:
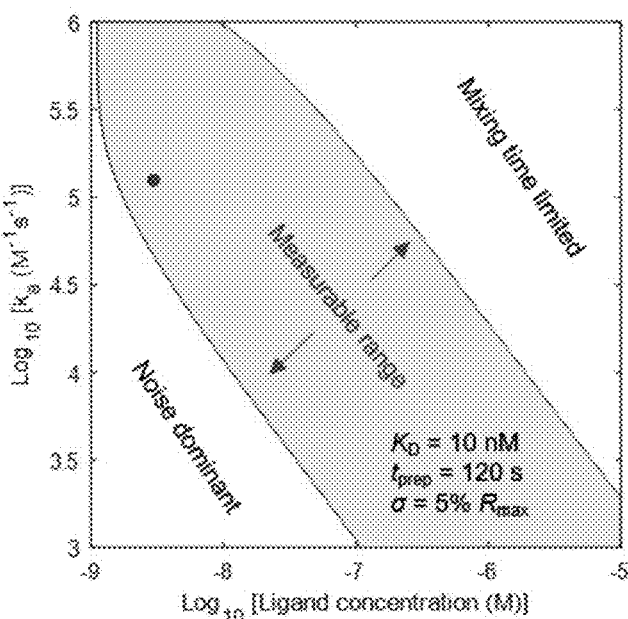
FIGS. 7A-7C. Simulations showing the limitation in binding kinetics measurement and possible improvements. (a) Simulation using experimental conditions for BSA-anti-BSA interaction (FIG. 5A). The shaded area marks the measurable range. The boundary of the shaded area is calculated using Eqs. 2 and 3, where the upper boundary line represents fast binding information lose due to sample preparation, and the lower boundary line is dominated by the noise level. $K_D$ used for the simulation is 10 nM, and the sample preparation time ($t_{prep}$) and measurement error ($\sigma$) are 120 s and 5% of the maximum response ($R_{max}$), respectively as determined from FIG. 3a. The single data point (dark grey dot) shows 2.3 nM anti-BSA with $k_a = 1.3 \times 10^5$ $M^{-1} \cdot s^{-1}$ (measured in FIG. 5A) is within the detection range. (b) The measurable range can be broadened by 2 orders of magnitude if $t_{prep}$ is reduced from 2 min to 1 s while keeping all the other parameters the same. (c) The measurable range would cover most of the typical molecular interactions with $t_{prep}$ reduced to 1 s and the measurement error reduced to 0.1% of $R_{max}$.

Based on the above analysis we evaluate and quantify the limitation of our technique. We first take the BSA and anti-BSA binding in FIG. 5A as an example. According to Eq. 3, the binding equilibrium is reached at $1-e^{-(k_ac+k_d)t} > 1-2\sigma$ considering the noise level $\sigma$, which is defined by the standard deviation in size measurement (p<0.05). For the BSA-anti-BSA binding, $\sigma$ is ~5% of the maximum response ($R_{max}$) and $K_D=k_d/k_a$ is ~10 nM. The kinetics is only distinguishable when the equilibrium is reached after the preparation time $t_{prep}=120$ s. Using these parameters, we calculate the measurable $k_a$ and c, which are mainly limited by the slow sample preparation. Another limitation is set by the signal-to-noise ratio (SNR). The signal should be greater than 20 at the end of measurement ($t_{end}=16$ min), namely $$\frac{c}{c+K_D}\left[1-e^{-(k_ac+k_d)t}\right] > 2\sigma,$$

so that it can be separated from the noise. By combining the two limitations, we obtain the $k_a$ dependent dynamic range, as shown in FIG. 7A. The measurable concentration range is about two orders of magnitude wide within 1 nM to 10 μM at common $k_a$ values (shaded region). The upper boundary line is limited by the sample preparation time and the lower one is due to insufficient SNR. Within the measurable range, higher ligand concentration is needed for slower binding reactions (small $k_a$) to achieve enough SNR, while lower concentration should be used for fast reactions (high $k_a$) to avoid early equilibrium. We also compare our experimental results in FIG. 5A with the calculation results in FIG. 7A. In the experiment, $k_a$ is determined to be $1.3 \times 10^5$ M$^{-1}$·s$^{-1}$, and 2.3 and 0.23 nM anti-BSA are measured. The 2.3 nM is within the measurable range (dot in FIG. 7A), and indeed shows sufficient SNR in the binding kinetic curve. The 0.23 nM is slightly beyond the measurable range, and has moderate SNR as predicted by the calculation. Because the above calculation is only valid with $K_D=10$ nM, we also plot $k_a$ vs c at different $K_D$ from 0.1 to 100 nM (data not shown). The measurable range does not change a lot, suggesting a variety of other interactions with different $K_D$ can be readily measured by our method.

Figure 7B:
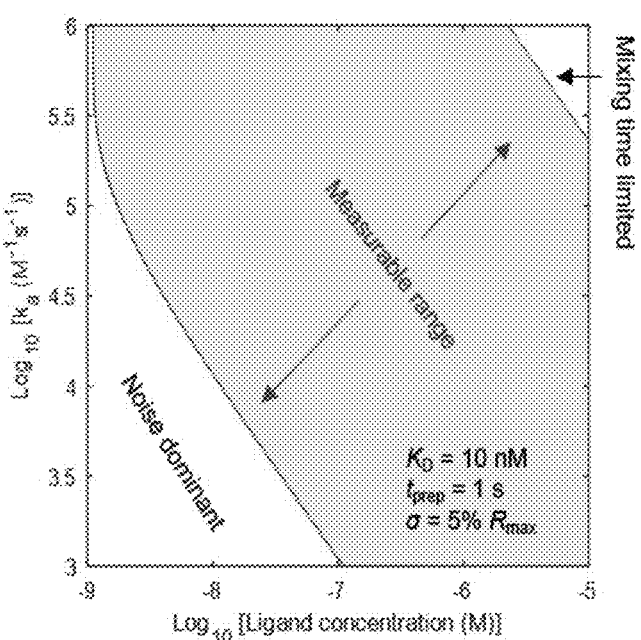
Figure 7C:
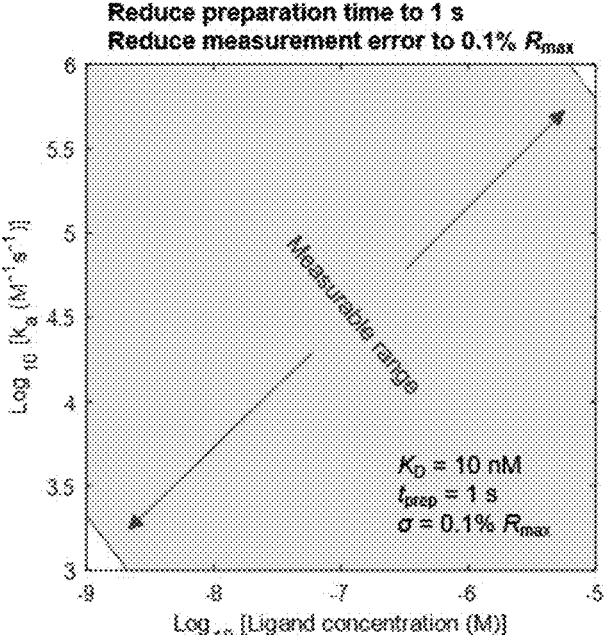

The calculation also allows us to investigate possible improvements to broaden the dynamic range. By reducing $t_{prep}$ from 2 min to 1 s, the measurable range can increase by two orders of magnitude (FIG. 7B). An additional decrease of $\sigma$ to 0.1% will further broaden the measurable range by an extra two orders of magnitude (FIG. 7C), making it cover almost all common molecular interactions. The preparation time could be saved by using microfluidic devices which provide fast mixing and well-controlled flow. And the noise could be lowered down by increasing particle counting number (see the noise analysis section). Currently, the noise is a statistical issue, but if we can track the same particles over a long period of time, the statistical issue can be circumvented, and the noise will be significantly reduced. In fact, many three-dimensional single particle tracking techniques have been developed to address this problem, which can be incorporated into our system.

CONCLUSION

We have developed a particle tracking based method to quantify protein-protein interactions. The protein of interest can be pulled down and separated from its original medium using magnetic nanoparticles, and the binding kinetics to ligand molecules is directly measured on the particle, without the need of elution and re-immobilization. We anticipate this method will simplify the traditional workflow for protein separation and detection and accelerate protein research.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. A method of determining molecular binding kinetics on particles, the method comprising:

contacting a sample that comprises a plurality of particle-bound biomolecules with a plurality of ligands that binds, or is capable of binding, to biomolecules of the plurality of particle-bound biomolecules to produce a particle-bound biomolecule-ligand composition that comprises one or more particle-bound biomolecule-ligand complexes, wherein a given particle-bound biomolecule in the plurality of particle-bound biomolecules comprises at least one particle bound to at least one biomolecule;

introducing an incident light toward the particle-bound biomolecule-ligand composition;

detecting light scattered from the particle-bound biomolecule-ligand complexes in the particle-bound biomolecule-ligand composition over a duration to produce a set of imaging data;

identifying and tracking trajectories of individual particle-bound biomolecule-ligand complexes across a sequence of image frames in the imaging data;

determining particle size information for the individual tracked complexes at multiple time points during the duration; and, determining molecular binding kinetics by computing time-dependent changes in the particle size information of the tracked complexes during ligand association events.

2. The method of claim 1, further comprising forming the particle-bound biomolecules by binding the biomolecules to the particles prior to contacting the sample with the plurality of ligands.

3. The method of claim 1, wherein the particles comprise nanoparticles.

4. The method of claim 1, wherein the particles are magnetic.

5. The method of claim 1, wherein the particle-bound biomolecule-ligand composition is disposed in at least one capillary.

6. The method of claim 1, wherein the set of imaging data comprises video data.

7. The method of claim 1, wherein the duration comprises about 15 minutes, about 10 minutes, about 5 minutes, or less time.

8. The method of claim 1, comprising detecting side scattered light from the particle-bound biomolecule-ligand complexes in the particle-bound biomolecule-ligand composition over the duration to produce the set of imaging data.

9. The method of claim 1, comprising tracking positions of the one or more of the particle-bound biomolecule-ligand complexes using the set of imaging data.

10. The method of claim 1, comprising tracking the positions of the one or more of the particle-bound biomolecule-ligand complexes in substantially real-time.

11. The method of claim 1, comprising quantifying an amount of interaction between the plurality of particle-bound biomolecules and the plurality of ligands.

12. The method of claim 1, wherein determining the size or volume changes of one or more of the particle-bound biomolecule-ligand complexes comprises determining hydrodynamic radii of the one or more of the particle-bound biomolecule-ligand complexes using the set of imaging data.

13. The method of claim 1, comprising producing the set of imaging data in the absence of separating the biomolecules and/or the ligands from the particle-bound biomolecule-ligand complexes prior to or concurrent with performing the contacting, introducing, or detecting steps.

14. The method of claim 1, wherein the particle-bound biomolecule-ligand complexes are label-free.

15. The method of claim 1, wherein the biomolecules and/or the ligands comprise proteins or nucleic acids.

16. A system for determining molecular binding kinetics on particles, comprising:

a sample container receiving area configured to receive a sample container that comprises a particle-bound biomolecule-ligand composition comprising a plurality of particle-bound biomolecules and a plurality of ligands that binds, or is capable of binding, to biomolecules of the plurality of particle-bound biomolecules to produce a particle-bound biomolecule-ligand composition that comprises one or more particle-bound biomolecule-ligand complexes, wherein a given particle-bound biomolecule in the plurality of particle-bound biomolecules comprises at least one particle bound to at least one biomolecule;

a light source configured to introduce an incident light toward the sample container receiving area;

a detector configured to collect light scattered from the particle-bound biomolecule-ligand complexes in the particle-bound biomolecule-ligand composition when the sample container is received in the sample container receiving area and the incident light is introduced from the light source; and a controller that comprises, or is capable of accessing, computer readable media comprising non-transitory computer-executable instructions which, when executed by at least one electronic processor, perform at least:

introducing the incident light from the light source toward the particle-bound biomolecule-ligand composition when the sample container is received in the sample container receiving area;

detecting light scattered from the particle-bound biomolecule-ligand complexes in the particle-bound biomolecule-ligand composition over a duration to produce a set of imaging data using the detector;

identifying and tracking trajectories of individual particle-bound biomolecule-ligand complexes across a sequence of image frames in the imaging data;

determining particle size information for the individual tracked complexes at multiple time points during the duration; and, determining molecular binding kinetics by computing time-dependent changes in the particle size information of the tracked complexes during ligand association events.

17. The system of claim 16, wherein the non-transitory computer-executable instructions which, when executed by the electronic processor, further perform at least: tracking positions of the one or more of the particle-bound biomolecule-ligand complexes using the set of imaging data.

18. The system of claim 16, wherein the non-transitory computer-executable instructions which, when executed by the electronic processor, further perform at least: tracking the positions of the one or more of the particle-bound biomolecule-ligand complexes in substantially real-time.

19

19. The system of claim 16, wherein the non-transitory computer-executable instructions which, when executed by the electronic processor, further perform at least: quantifying an amount of interaction between the plurality of particle-bound biomolecules and the plurality of ligands.

20. A computer readable media comprising non-transitory computer executable instruction which, when executed by at least electronic processor, perform at least:

introducing an incident light from a light source toward a sample container that comprises a particle-bound biomolecule-ligand composition comprising a plurality of particle-bound biomolecules and a plurality of ligands that binds, or is capable of binding, to biomolecules of the plurality of particle-bound biomolecules to produce a particle-bound biomolecule-ligand composition that comprises one or more particle-bound biomolecule-ligand complexes, wherein a given particle-bound biomolecule in the plurality of particle-bound biomolecules comprises at least one particle bound to at least one biomolecule;

detecting light scattered from the particle-bound biomolecule-ligand complexes in the particle-bound biomolecule-ligand composition over a duration to produce a set of imaging data using the detector;

identifying and tracking trajectories of individual particle-bound biomolecule-ligand complexes across a sequence of image frames in the imaging data;

determining particle size information for the individual tracked complexes at multiple time points during the duration; and, determining molecular binding kinetics by computing time-dependent changes in the particle size information of the tracked complexes during ligand association events.

* * * * *